United States Patent [19]
Hubbs

[11] Patent Number: 6,022,719
[45] Date of Patent: Feb. 8, 2000

[54] ENZYMATIC PROCESS FOR THE MANUFACTURE OF ASCORBIC ACID, 2-KETO-L-GULONIC ACID AND ESTERS OF 2-KETO-L-GULONIC ACID

[75] Inventor: John Clark Hubbs, Kingsport, Tenn.

[73] Assignee: Eastman Chemical Company, Kingsport, Tenn.

[21] Appl. No.: 09/140,933

[22] Filed: Aug. 27, 1998

Related U.S. Application Data

[62] Division of application No. 08/845,295, Apr. 25, 1997, Pat. No. 5,817,490
[60] Provisional application No. 60/017,879, May 17, 1996.
[51] Int. Cl.$^7$ .......................................................... C12P 7/60
[52] U.S. Cl. ........................ 435/138; 435/135; 435/195; 435/197; 435/219
[58] Field of Search ..................................... 435/138, 195, 435/197, 219

[56] References Cited

U.S. PATENT DOCUMENTS

| | | | |
|---|---|---|---|
| 2,301,811 | 11/1942 | Reichstein | 260/344 |
| 5,008,193 | 4/1991 | Anderson et al. | 435/138 |
| 5,441,882 | 8/1995 | Estell et al. | 435/222 |
| 5,817,490 | 10/1998 | Hubbs | 435/195 |

FOREIGN PATENT DOCUMENTS

| | | |
|---|---|---|
| 0 207 763 | 1/1987 | European Pat. Off. . |
| 0 292 303 | 11/1988 | European Pat. Off. . |
| 0 401 704 | 12/1990 | European Pat. Off. . |
| 0 514 694 A1 | 4/1992 | European Pat. Off. . |
| 466548 | 6/1937 | United Kingdom . |
| WO 85/01745 | 4/1985 | WIPO . |
| 87/00839 | 2/1987 | WIPO . |

OTHER PUBLICATIONS

D. G. Hayes, "The Catalytic Activity of Lipases Toward Hydroxy Fatty Acids—A Review", *Journal of the American Oil Chemists' Society*, vol. 73, No. 5, pp. 543–549, May 1, 1996.

T. Reichstein et al., *Helv. Chim. Acta,* vol. 17, pp. 311–328 (1934).
T. Sonoyama et al., *Applied and Envtl. Microbiology,* vol. 43, pp. 1064–1069 (1982).
S. Anderson et al., *Science,* vol. 230, pp. 144–149 (1985).
M. Shinjoh et al., *Applied and Envtl. Microbiology,* vol. 61, pp. 413–420 (1995).
Yamazaki, *J. Agri. Chem. Soc. Japan,* vol. 28, pp. 890–894 (1954) (translation not included).
*Chemical Abstracts,* vol. 50, 5992d.
F. Thiel, *Catalysis Today,* pp. 517–536 (1994).
A. L. Gutman et al., *Tetrahedron Lett.,* vol. 28, pp. 3861–3864 (1987).
A. L. Gutman et al., *Tetrahedron Lett.,* vol. 28, pp. 5367–5368 (1987).
*Enzyme Nomenclature* (Academic Press, 1992) (cover pages only).
E. L. Smith et al., *J. Biol. Chem.,* vol. 243, pp. 2184–2191 (1968).
M. Matsushima et al., *FEBS Lett.,* vol. 293, pp. 37–41 (1991).
J. Uppenberg et al., *Structure,* vol. 2, pp. 293–308, 453 (1994).
H. J. Duggleby et al., *Nature,* vol. 373, pp. 264–268 (1995).
*Molecular Cloning—A Laboratory Manual,* Cold Spring Harbor Laboratory Press, N.Y. (1989), vol. 1, 2, and 3 (title pages and tables of contents only).
*Current Protocols in Molecular Biology,* F. M. Ausubel et al., editors, Greene Publishing Associates and Wiley–Interscience, N.Y. (1989) (title pages and table of contents only).

*Primary Examiner*—Herbert J. Lilling
*Attorney, Agent, or Firm*—Cheryl J. Tubach; Harry J. Gwinnell

[57] ABSTRACT

The present invention is directed toward efficient, high-yield processes for making ascorbic acid, 2-keto-L-gulonic acid, and esters of 2-keto-L-gulonic acid. The processes comprise reacting the appropriate starting materials with a hydrolase enzyme catalyst such as a protease, an esterase, a lipase or an amidase.

4 Claims, No Drawings

ENZYMATIC PROCESS FOR THE MANUFACTURE OF ASCORBIC ACID, 2-KETO-L-GULONIC ACID AND ESTERS OF 2-KETO-L-GULONIC ACID

CROSS REFERENCE TO RELATED APPLICATIONS

This is a divisional application of application Ser. No. 08/845,295, filed Apr. 25, 1997 now U.S. Pat. No. 5,817,490 which claims the benefit of U.S. Provisional Application No. 60/017,879, filed May 17, 1996.

FIELD OF THE INVENTION

This invention relates to processes for the manufacture of ascorbic acid, 2-keto-L-gulonic acid (KLG), and esters of KLG. More particularly, the present invention relates to the use of enzyme catalysts in the manufacture of ascorbic acid, KLG or esters of KLG.

BACKGROUND OF THE INVENTION

Ascorbic acid, also known as vitamin C, is a dietary factor which must be present in the human diet to prevent scurvy and which has been identified as an agent that increases resistance to infection. Ascorbic acid is used commercially, for example, as a nutrition supplement, color fixing agent, flavoring and preservative in meats and other foods, oxidant in bread doughs, abscission of citrus fruit in harvesting and reducing agent in analytical chemistry.

One current method for the manufacture of ascorbic acid utilizes a modification of the original Reichstein-Grossner synthesis (Reichstein et al., *Helv. Chim. Acta*, 17:311 (1934); U.S. Pat. No. 2,301,811 to Reichstein; all references cited herein are specifically incorporated by reference). In this process a glucose source is converted to ascorbic acid. During conversion an intermediate of a diacetonide of KLG is produced.

Several two stage methods exists for the manufacture of ascorbic acid. In the first stage, glucose is converted via fermentation processes to either an isolated intermediate of KLG (Sonoyama et al., *Applied and Envtl. Microbiology*, 43:1064–1069 (1982); Anderson et al., *Science*, 230:144–149 (1985); Shinjoh et al., *Applied and Envtl. Microbiology*, 61:413–420 (1995)) or the intermediate of the Reichstein-Grossner synthesis, the diacetonide of KLG.

The second stage, which converts either of the intermediates to ascorbic acid, proceeds by one of two reported routes. The first route, a modification of the latter steps of the Reichstein-Grossner synthesis, requires a multitude of steps whereby the intermediate is esterified with methanol under strongly acidic conditions to produce methyl-2-keto-L-gulonate (MeKLG). The MeKLG is then reacted with base to produce a metal ascorbate salt. Finally, the metal ascorbate salt is treated with an acidulant to obtain ascorbic acid. The second route is a one-step method comprising acid-catalyzed cyclization of KLG, as originally disclosed in GB Patent No. 466548 to Reichstein) and later modified by Yamazaki (Yamazaki, *J. Agri. Chem. Soc. Japan*, 28:890–894 (1954), and *Chem. Abs.*, 50:5992d) and again by Yodice (WO 87/00839). The Yodice method is commercially undesirable because it uses large amounts of gaseous hydrogen chloride, requires very expensive process equipment and produces an ascorbic acid product requiring extensive purification.

Lipases, a group of hydrolase enzymes, have been used with some success in the synthesis of esters of organic acids. In particular, lipases have been utilized in the transesterification of alcohols in which the esterifying agent is irreversible, such as when vinyl acetate is used as the esterifying agent (Thiel, *Catalysis Today*, 517–536 (1994)). Gutman et. al., *Tetrahedron Lett.*, 28:3861–3864 (1987), describes a process for preparing simple 5-membered ring lactones from gamma-hydroxy methyl esters using porcine pancreatic lipase as the catalyst. However, Gutman et al., *Tetrahedron Lett.*, 28:5367–5368 (1987), later reported that substituting delta-hydroxy methyl esters for gamma-hydroxy methyl esters and using the same catalyst produced only polymers. In EP 0 515 694 A1 to Sakashita et. al., a synthesis of esters of ascorbic acid, which are acylated on the primary hydroxyl group, comprises reacting ascorbic acid with a variety of fatty acid active esters (i.e., fatty acid vinyl esters) in a polar organic solvent in the presence of a lipase.

Thus, there exists a need in the art for methods of producing (a) ascorbic acid or metal salts thereof from KLG or esters of KLG, (b) KLG from esters of KLG and (c) esters of KLG from KLG, which have high yield and high purity with little or no by-product formation and are conducted under mild conditions. Accordingly, it is to the provision of such that the present invention is primarily directed.

SUMMARY OF THE INVENTION

The present invention discloses an advancement in the chemical and biological arts in which a process for preparing ascorbic acid comprises contacting KLG or an ester of KLG with a hydrolase enzyme catalyst.

In another embodiment of the present invention, a process for producing KLG comprises contacting an ester of KLG in an aqueous solution with a hydrolase enzyme catalyst.

In still another embodiment of the present invention, a process for producing esters of KLG from KLG comprises contacting an alcoholic solution of KLG with a hydrolase enzyme catalyst. The alcoholic solution contains an alcohol corresponding to an alkyl moiety of the ester of KLG to be prepared.

In still another embodiment of the present invention, a process for producing esters of KLG from esters of KLG comprises contacting an alcoholic solution of a first ester of KLG with a hydrolase enzyme catalyst. The alcoholic solution contains an alcohol corresponding to an alkyl moiety of a second ester of KLG which is to be prepared.

DETAILED DESCRIPTION OF THE INVENTION

The present invention is directed to the unexpected discovery that ascorbic acid can be formed from KLG or, more preferably, esters of KLG by inducing ring closure of KLG or esters of KLG using a hydrolase enzyme as a catalyst. The process for producing the ascorbic acid may be performed in the melt or in solution. The process may also be performed in vivo or in vitro. For in vivo processes, the hydrolase enzyme catalyst may be naturally occurring within a host cell or may be introduced into a host cell or organism by recombinant DNA methods.

The present invention is also directed to the unexpected discovery that KLG can be prepared in a reversible reaction by reacting an ester of KLG in an aqueous solution using a hydrolase enzyme as a catalyst. Moreover, the present invention is directed to the unexpected discovery that an ester of KLG can be prepared by reacting KLG or another ester of KLG in an alcoholic solution using a hydrolase enzyme as a catalyst. The alcohol used to prepare the solution corresponds to the alkyl moiety of the ester of KLG being prepared.

licheniformis. Preferred proteases are those containing at least 70% sequence homology with Subtilisin. Proteases having sequence homology with Subtilisin are used in the detergent industry and, therefore, are readily available. More preferred are proteases having at least 80% sequence homology with Subtilisin, even more preferred are proteases having at least 90% sequence homology with Subtilisin and, in particular, proteases having at least 95% sequence homology to Subtilisin. A highly preferred protease is Subtilisin itself having an amino acid sequence (SEQ ID NO: 1) described by Smith et al., *J. Biol. Chem.*, 243:2184–2191 (1968), and given below:

| MMRKKSFWLG | MLTAFMLVFT | MAFSDSASAA | QPAKNVEKDY |
| IVGFKSGVKT | ASVKKDIIKE | SGGKVDKQFR | IINAAKAKLD |
| KEALKEVKND | PDVAYVEEDH | VAHALAQTVP | YGIPLIKADK |
| VQAQGFKGAN | VKVAVLDTGI | QASHPDLNVV | GGASFVAGEA |
| YNTDGNGHGT | HVAGTVAALD | NTTGVLGVAP | SVSLYAVKVL |
| NSSGSGTYSG | IVSGIEWATT | NGMDVINMSL | GGPSGSTAMK |
| QAVDNAYARG | VVVVAAAGNS | GSSGNTNTIG | YPAKYDSVIA |
| VGAVDSNSNR | ASFSSVGAEL | EVMAPGAGVY | STYPTSTYAT |
| LNGTSMASPH | VAGAAALILS | KHPNLSASQV | RNRLSSTATY |
| LGSSFYYGKG | LINVEAAAQ. | | |

The hydrolase enzymes for use as catalysts in the processes of the present invention may be derived from or isolated from any appropriate source organisms. Examples of which include, but are not limited to, plants, microorganisms, and animals, such as yeast, bacteria, mold, fungus, birds, reptiles, fish, and mammals. Hydrolase enzymes for the purposes of this invention are defined generally by the enzyme class E.C.3.-.-.-, as defined in *Enzyme Nomenclature* (Academic Press, 1992), and are commercially available.

Preferred hydrolase enzymes are those capable of effecting hydrolysis of molecules containing carbonyl or phosphate groups. More specifically, the preferred hydrolases are capable of effecting hydrolysis at a carbonyl carbon bearing a heteroatom single bond. Examples of such carbonyl carbons bearing a heteroatom single bond include, but are not limited to, esters, thioesters, amides, acids, acid halides, and the like. The preferred hydrolases include the enzyme class E.C.3.1.-.-, which includes hydrolases acting on ester bonds, such as esterases and lipases; the enzyme class E.C.3.2-.-, which includes glycosidases; the enzyme class E.C.3.4-.-, which includes peptide hydrolases, such as proteases; and the enzyme class E.C.3.5.-.-, which includes amidases acting on bonds other than peptide bonds. Most preferred hydrolases include proteases, amidases, lipases, and esterases.

More preferred hydrolases contain an active site serine residue which is capable of undergoing esterification or transesterification with KLG or esters of KLG. Even more preferred are those hydrolases which contain the catalytic triad of serine, histidine and apartic acid.

Preferred proteases include those derived from bacteria of the genera Bacillus or Aspergillus. Particularly preferred proteases are those obtained from the bacteria *Bacillus*

For the convenience of the reader, Table 1 provides a summary of amino acid shorthand used above and in the remainder of the specification.

TABLE 1

| Amino Acid Symbol | Three-Letter Abbreviation | One-Letter |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Also encompassed by the scope of the present invention are proteases corresponding to one to six site-specific mutants, sequence additions, and sequence deletions of the sequence given above. Even more preferred are proteases corresponding to zero to two site-specific mutants of the Subtilisin sequence given above.

Esterases suitable for the present invention include those obtained from pig liver extract. Preferred esterases are those having at least 70% sequence homology with pig liver esterase having an amino acid sequence (SEQ ID NO: 2) described in Matsushima et al., *FEBS Lett.*, 293:37 (1991), and given below:

| | | | |
|---|---|---|---|
| MWLLPLVLTS | LASSATWAGQ | PASPPVVDTA | QGRVLGKYVS |
| LEGLAFTQPV | AVFLGVPFAK | PPLGSLRFAP | PQPAEPWSFV |
| KNTTSYPPMC | CQDPVVEQMT | SDLFTNFTGK | ERLTLEFSED |
| CLYLNIYTPA | DLTKRGRLPV | MVWIHGGGLV | LGGAPMYDGV |
| VLAAHENFTV | VVVAIQYRLG | IWGFFSTGDE | HSRGNWGHLD |
| QVAALHWVQE | NIANFGGDPG | SVTIFGESFT | AGGESVSVLV |
| LSPLAKNLFH | RAISESGVAL | TVALVRKDMK | AAAKQIAVLA |
| GCKTTTSAVF | TFVHCLRQKS | EDELLDLTLK | MKFLTLDFHG |
| DQRESHPFLP | TVVDGVLLPK | MPEEILAEKD | FTFNTVPYIV |
| GINKQEFGWL | LPTMMGFPLS | EGKLDQKTAT | SLLWKSYPIA |
| NIPEELTPVA | TFTDKYLGGT | DDPVKKKDLF | LDLMGDVVFG |
| VPSVTVARQH | RDAGAPTYMY | EFQYRPSFSS | DKFTKPKTVI |
| GDHGDEIFSV | FGFPLLKGDA | PEEEVSLSKT | VMKFWANFAR |
| SGNPNGEGLP | HWPFTMYDQE | EGYLQIGVNT | QAAKRLKGEE |
| VAFWNDLLSK | EAAKKPPKIK | HAEL. | |

Esterases more preferably have at least 80% sequence homology with the sequence of the pig liver esterase given above, even more preferably at least 90% sequence homology, especially preferred at least 95% sequence homology. Highly preferred is the pig liver esterase having the sequence given above.

Also encompassed by the scope of the present invention are esterases corresponding to one to six site-specific mutants, sequence additions, and sequence deletions of the sequence given above. Even more preferred are esterases corresponding to zero to two site-specific mutants of the pig liver esterase sequence given above.

Preferred lipases include those isolated from pigs and other mammals, microorganisms, and plants. This includes, but is not limited to, lipases obtained from the genera Aspergillus, Mucor, Candida, Pseudomonas, Humicola, Rhizopus, Chromobacterium, Alcaligenes, Geotricum, and Penicillium. Preferred lipases also include extracellular lipases, such as cutinases. More preferred lipases have at least 70% sequence homology with Candida Antartica type B lipase, even more preferred have at least 80% sequence homology, still more preferred have at least 90% sequence homology, and even more preferred have at least 95% sequence homology. A highly preferred lipase is the Candida Antartica type B lipase itself which has an amino acid sequence (SEQ ID NO: 3) described by Uppenberg et al., Structure, 2:293, 453 (1994), and given below:

| | | | |
|---|---|---|---|
| MKLLSLTGVA | GVLATCVAAT | PLVKRLPSGS | DPAFSQPKSV |
| LDAGLTCQGA | SPSSVSKPIL | LVPGTGTTGP | QSFDSNWIPL |
| STQLGYTPCW | ISPPPFMLND | TQVNTEYMVN | AITALYAGSG |
| NNKLPVLTWS | QGGLVAQWGL | TFFPSIRSKV | DRLMAFAPDY |
| KGTVLAGPLD | ALAVSAPSVW | QQTTGSALTT | ALRNAGGLTQ |
| IVPTTNLYSA | TDEIVQPQVS | NSPLDSSYLF | NGKNVQAQAV |
| CGPLFVIDHA | GSLTSQFSYV | VGRSALRSTT | GQARSADYGI |
| TDCNPLPAND | LTPEQKVAAA | ALLAPAAAAI | VAGPKQNCEP |
| DLMPYARPFA | VGKRTCSGIV | TP. | |

Also encompassed by the scope of the present invention are lipases corresponding to one to six site-specific mutants, sequence additions, and sequence deletions of the sequence given above. Even more preferred are lipases corresponding to zero to two site-specific mutants of the Candida Antartica type B sequence given above.

Preferred amidases include those isolated from bacteria of the genus Penicillium. A more preferred amidase has at least 80% sequence homology with Penicillin acylase. A particularly preferred amidase is Penicillin acylase, which is also referred to as Penicillin amidohydrolase, E.C. 3.5.1.11 (Duggleby et al., Nature, 373:264–268 (1995)).

For hydrolases containing serine at their active site, the first step in the reaction of either KLG or esters of KLG is believed to involve formation of a KLG-enzyme ester via acylation by KLG of the active site serine. Intra-molecular ring closure is believed to yield ascorbic acid (or its salts), whereas alcoholysis yields an ester of KLG and hydrolysis yields KLG.

The process of the present invention comprises contacting either KLG or an ester of KLG with a hydrolase enzyme to form ascorbic acid. Preferably, this reaction is performed in the presence of an organic solvent system, an aqueous solvent system or a mixture thereof. The organic solvent is preferably a $C_1$–$C_6$ alcohol. The aqueous solvent system or mixed aqueous and organic solvent systems are more preferable because ascorbic acid, KLG, and esters of KLG are generally more soluble in aqueous solvent systems. For the in vitro production of ascorbic acid from esters of KLG, the mixed aqueous and organic solvent systems or organic solvent systems are preferable to minimize competing hydrolysis reactions which can produce KLG as a byproduct. Aqueous solvent systems are especially preferable when utilizing whole cell systems for the production of ascorbic acid in vivo.

In one aspect of the present invention, the ascorbic acid is produced from KLG or esters of KLG in in vivo, whole cell, and whole organism production systems in the presence of the hydrolase enzyme catalyst. In one embodiment, the hydrolase enzyme is naturally produced by the host organism. In another embodiment, the hydrolase enzyme is produced by the host organism through recombinant DNA technology. For example, a gene sequence encoding a hydrolase enzyme is inserted in a host organism wherein the host organism may be a microorganism, plant, or animal which is capable of expressing the hydrolase enzyme. The host organism producing the hydrolase enzyme is cultured, i.e. provided with nutrients and a suitable environment for growth, in the presence of KLG or esters of KLG to produce the ascorbic acid. Preferably, the host organism is Pantoea citrea, previously referred to as *Erwinia herbicola* as disclosed in U.S. Pat. No. 5,008,193 to Anderson et al.

Also preferably, the host organism is one that produces KLG in addition to producing the hydrolase enzyme. Representative organisms are from the genera Pantoea or Gluconobacter, such as disclosed in Shinjoh et al., *Applied and Envtl. Microbiology*, 61:413–420 (1995), and the genus Corynebacterium as disclosed in Sonoyama et al., *Applied and Envtl. Microbiology*, 43:1064–1069 (1982).

As used herein, recombinant DNA technology includes in vitro recombinant DNA techniques, synthetic techniques and in vivo recombinant/ genetic recombination and is well known in the art. See, for example, the techniques described in Maniatis et al., *Molecular Cloning A Laboratory Manual*, Cold Spring Harbor Laboratory, N.Y. (1989); Ausubel et al., *Current Protocols in Molecular Biology*, Greene Publishing Assoc. and Wiley Interscience, N.Y. (1989); Anderson et al., *Science*, 230:144–149 (1985); and U.S. Pat. No. 5,441,882 to Estell et. al.

For preparations of KLG from esters of KLG, an aqueous solution of the ester of KLG is reacted with the hydrolase enzyme. A co-solvent may be used in the preparation of KLG and is preferably a $C_1$–$C_6$ alcohol.

For preparations of the esters of KLG from KLG or from other esters of KLG, the starting material is in an alcoholic solution wherein the alcohol corresponds to the alkyl moiety of the ester of KLG to be prepared. The alkyl moiety R of the alcohol ROH from which the preferred ester of KLG is derived may be chosen from branched or straight chain, saturated or unsaturated, alkyl, arylalkyls, aryls, and substituted aryls. Preferred R groups include $C_1$ to $C_6$ straight or branched chain, saturated or unsaturated alkyls. Even more preferred esters of KLG that are derived for alkyl moieties include MeKLG, ethyl-KLG, n-propyl-KLG, isopropyl-KLG, n-butyl-KLG, isobutyl-KLG, t-butyl-KLG, and n-pentyl-KLG. The most preferred esters of KLG produced are MeKLG due to its ease of manufacture and butyl-KLG due to the advantageous use of the butanol water azeotroph in water removal. A co-solvent may be used in the preparation of the esters of KLG and is preferably water, a $C_1$–$C_6$ alcohol or a mixture thereof.

Preferred temperatures for conducting the reactions of the present invention are from about 5° C. to about 120° C. Even more preferred temperatures are from about 25° C. to about 100° C., and especially preferred temperatures are from about 38° C. to about 80° C.

The preferred pH for the process of the present invention is between about 1.5 and about 10, and a more preferred pH is between about 3 and about 10. For the preparation of ascorbic acid salts from esters of KLG, a particularly preferred pH range is between about 6 and about 10. For the preparation of ascorbic acid as the free acid, a preferred pH is that under the pKa of ascorbic acid and, more preferred, is that under about 4.2. For the preparation of KLG from esters of KLG, a particularly preferred pH range is between about 5 and about 10 due to the generally enhanced rates of enzyme assisted hydrolysis in this pH range. Alternatively, a pH of between about 1.5 and about 2.5 is particularly desirable for the generation of KLG in protonated form. Finally, for the preparation of esters of KLG from KLG, a particularly preferred pH range is between about 3 and about 6.

Each hydrolase has a temperature optimum, a pH optimum, and a pH and temperature range associated with activity. Thus, the appropriate pH and temperature range for a given hydrolase is that which allows for activity of the hydrolase and avoids conditions which are denaturing or inactivating to the hydrolase. For conditions which may be denaturing, such as high temperature or the use of denaturing solvents such as methanol or the like, a minimal amount of testing may be required to define those hydrolases which remain active under a given set of conditions.

The following examples are offered by way of illustration and are not intended to limit the scope of the claimed invention.

EXAMPLES

Proton and carbon nuclear magnetic resonance (NMR) spectra were recorded on a Varian Gemini 300 NMR instrument operating at 300 MHZ in proton mode and 75 MHZ in carbon mode. All NMR spectra were referenced to tetramethylsilane (TMS) at 0 parts per million (ppm) and peak frequencies were recorded in ppm unless otherwise specified. HPLC (high-performance liquid chromatography) analysis was carried out using ultraviolet (UV) detection. Mass spectra (MS) were obtained using a Fisons VG Analytical Ltd. Autospec Mass Spectrometer in FD (field desorption) mode.

The KLG used in the experiments was obtained by fermentation according to the method of Lazarus et. al., Anderson et al., *Science*, 230:144–149 (1985), and was purified by concentration and crystallization. KLG may alternatively be prepared by chemical conversion from L-sorbose according to methods well known in the art (see e.g., U.S. Pat. No. 2,301,811 to Reichstein). A standard of methyl-2-keto-L-gulonate was purchased from Aldrich Chemical Company (Rare and Specialty Chemicals Catalog), in addition to being prepared by esterification of KLG by methods similar to the procedure used for the preparation of butyl-KLG, described below.

Enzyme hydrolase samples were obtained from commercial sources, including Sigma Chemical Company, Altus Biologics, Recombinant Biocatalysis, Boehringer Mannheim, Novo Nordisk, Genencor International, Thermogen, and Fluka.

Example 1

This example describes the preparation and purification of butyl 2-keto-L-gulonate.

KLG hydrate (51.62 g) was charged in a 500 ml reaction vessel under argon. The reactor was equipped with a 12" vigreux column attached to a Dean Stark trap. The reactor was then charged with n-butanol (310 g) and p-toluene sulfonic acid (2.3 g). The reaction mixture was brought to reflux (81–82° C.) under mild vacuum (approximately 150 mm Hg) with stirring. Reflux was maintained for a total of two hours and 40 minutes. Heating was discontinued. The reaction was allowed to cool and remain at room temperature for approximately 3 days. The resulting crystals were filtered through a coarse fritted glass filter and washed with two portions of n-butyl alcohol (139 g followed by 37 g). The resulting solids (24.4 g) were dissolved in hot ethyl acetate (250 ml) and recrystallized by standing overnight at room temperature. The recrystallized butyl-KLG was isolated by filtration and dried under vacuum (1.5 mm Hg) until constant weight (15.97 g) was achieved.

The butyl-KLG thus prepared was found to have a solubility of at least 50 weight percent in water as it was soluble at all concentrations under 50 weight percent in water. The recrystallized butyl-KLG of this example had satisfactory proton and carbon NMR spectra and gave the predicted molecular weight by field desorption mass spectrometry.

$^1$H NMR (DMSO, digital resolution=0.11 Hz, TMS at half height=0.5 Hz): 6.49 (OH, d, J=1.4 Hz), 4.96 (OH, d, J=5.0 Hz), 4.84 (OH, d, J=4.8 Hz), 4.78 (OH, d, J=7.4 Hz), 4.17–4.0 (m, 2 H), 3.5–3.2 (m, approximately 5 H), 1.64–1.5 (m, 2 H), 1.4–1.35 (m, 2 H), 0.89 (CH$_3$ , t, J=7.3).

$^{13}$C NMR (DMSO, decoupled): 169.4, 96.3, 73.8, 72.8, 69.8, 64.5, 62.8, 30.0, 18.4, 13.5.

FDMS: M=250

Example 2

The following procedure was used to demonstrate enzymes for activity under specific pH and aqueous solvent composition conditions.

Initial enzyme screens were carried out as follows. Enzyme (typically 10 mg), aqueous buffer (typically 860 microliters (ul) or 550 ul), aqueous 0.2 M CaCl$_2$ (10 ul), methanol (typically 90 ul or 400 ul), and an aqueous solution of substrate (typically 90 ul of butyl-KLG at a typical concentration of 1100,000 ppm) were added to a 2 ml polypropylene centrifuge tube. The resulting solution was vortexed briefly and placed on a shaker bath at 300 rpm at 38° C. (typically for 18 hours or more). After incubation, samples were centrifuged at 14,000 G's (14,000 times gravity) for 20 minutes to remove enzyme, sampled (300 ul), and diluted to one milliliter with distilled water. If not analyzed by HPLC within the day, samples were frozen prior to analysis.

Summarized below in Table 2 is the HPLC data of the products (and remaining substrate) upon reaction of butyl-KLG (BuKLG) with a variety of enzyme hydrolases in water/methanol solution. The data were reported in terms of parts per million of KLG, MeKLG, ascorbic acid (ASA) and butyl-KLG. The reporting of a 0 (zero) indicated that the amount of material present was below the detection threshold of the instrument. Samples labeled as "no enzyme" were controls within a given run. The controls contained substrate but no enzyme and thus represented experimental and HPLC background data.

TABLE 2

Enzyme Screen for Hydrolysis/Methanolysis of Butyl-KLG (38° C. for 41 Hours/38% Methanol-Water/0.1 MES Buffer)

| Enzyme | Measured, pH | KLG | MeKLG | ASA | BuKLG (ppm) |
|---|---|---|---|---|---|
| ESL-001-01 | 5.8 | 1180 | 2352 | 766 | 4603 |
| ESL-001-02 | 5.6 | 704 | 1084 | 302 | 7736 |
| ESL-001-03 | 5.7 | 386 | 527 | 257 | 8931 |
| ESL-001-04 | 5.8 | 550 | 752 | 833 | 6229 |
| ESL-001-05 | 5.9 | 456 | 684 | 469 | 7942 |
| ESL-001-06 | 5.6 | 547 | 661 | 129 | 8896 |
| ESL-001-07 | 5.7 | 311 | 755 | 489 | 6540 |
| No Enzyme | | 108 | 325 | 33 | 10177 |
| No Enzyme (repeat) | | 107 | 303 | 0 | 9459 |
| No Enzyme | | 117 | 327 | 42 | 9878 |
| No Enzyme (repeat) | | 103 | 269 | 2 | 8593 |
| No Enzyme | | 116 | 322 | 0 | 9473 |

Table 2 illustrates that the hydrolases provided by Recombinant Biocatalysis (ESL-001-01 through ESL-001-07) showed appreciable conversion of butyl-KLG to ascorbic acid, MeKLG, and KLG in a 38% methanol-water solution buffered with morpholinoethane sulfonic acid (MES) hemisodium salt at a pH controlled between 5.5 and 6. These hydrolase enzymes are sold commercially by Recombinant Biocatalysis as recombinant esterases and lipases from thermophilic organisms under the tradename CloneZyme™.

Example 3

Table 3 below illustrates that a variety of acylases, esterases, lipases, and proteases showed appreciable conversion of butyl-KLG to ascorbic acid, MeKLG, and KLG in a 38% methanol-water solution buffered at pH 4.8 to 5.8 with MES buffer. The enzymes labeled as ChiroClec™ are crystalline crosslinked enzymes sold commercially by Altus Biologics. ChiroClec™ -CR is a lipase from *Candida rugosa*, ChiroClec™ -BL is a crystalline form of Subtilisin (a protease), and ChiroClec™ -PC is a lipase from *Pseudomonas cepacia*. *Candida Antartica* B (a lipase), pig liver esterase (a hydrolase), and *Bacillus Species* protease showed particularly high levels of activity.

TABLE 3

Enzyme Screen for Hydrolysis/Methanolysis of Butyl-KLG (38° C. for 16 Hours/38% Methanol-Water/0.1M MES Buffer)

| Enzyme | Measured pH | KLG | MeKLG | ASA | BuKLG (ppm) |
|---|---|---|---|---|---|
| Pig Liver Esterase | 5.3 | 446 | 4377 | 294 | 5711 |
| Pseudomonas cepacia Lipase | 5.3 | 98 | 295 | 65 | 11355 |
| Porcine Pancreatic Lipase | 5.4 | 81 | 316 | 49 | 10709 |
| Candida Rugosa Lipase | 5.7 | 122 | 197 | 180 | 10689 |
| Alpha-Chymotrypsin | 4.9 | 57 | 152 | 20 | 11174 |
| Penicillin Acylase | 5.6 | 83 | 1307 | 15 | 12007 |
| Aspergillus niger Lipase | 5.7 | 302 | 541 | 55 | 12290 |
| no enzyme | 5.1 | 88 | 210 | 5 | 10393 |
| no enzyme | 5.1 | 87 | 199 | 1 | 11553 |
| Candida Antartica 'A' Lipase | 5.4 | 88 | 242 | 37 | 10670 |
| Candida lipolytica Lipase | 5.3 | 91 | 92 | 5 | 11604 |
| Candida antartica 'B' Lipase | 4.8 | 2915 | 6807 | 0 | 0 |
| Humicola lanuginosa Lipase | 5 | 63 | 90 | 6 | 10191 |
| Bacillus Species Protease | 4.8 | 2587 | 5386 | 9 | 1251 |

TABLE 3-continued

Enzyme Screen for Hydrolysis/Methanolysis of Butyl-KLG
(38° C. for 16 Hours/38% Methanol-Water/0.1M MES Buffer)

| Enzyme | Measured pH | KLG | MeKLG | ASA | BuKLG (ppm) |
|---|---|---|---|---|---|
| no enzyme | 5.2 | 94 | 194 | 1 | 11552 |
| ChiroCLEC-CR (Dry) | 5.1 | 113 | 222 | 2 | 10988 |
| ChiroCLEC-BL (Dry) | 5.4 | 194 | 642 | 3 | 5123 |
| ChiroCLEC-PC (Pseudomonas cepacia) | 5.7 | 147 | 566 | 1 | 10471 |
| Rhizoipus Delmar Lipase | 5.5 | 51 | 99 | 1 | 7392 |
| Rhizopus Niveus Lipase | 5.1 | 80 | 252 | 17 | 10453 |
| Rhizopus Oryzae Lipase | 5.5 | 58 | 172 | 5 | 10873 |
| Chromobacterium Viscosum Lipase | 5.5 | 433 | 187 | 1 | 10843 |
| Geotricum Candidum Lipase | 5 | 33 | 407 | 7 | 10000 |
| Mucor Javanicus Lipase | 5.5 | 33 | 167 | 97 | 9950 |
| Aspergillus Oryzae Protease | 5.8 | 289 | 781 | 96 | 7429 |
| Amano-Lipase PS30 (Pseudomonas) | 5.3 | 56 | 300 | 49 | 9143 |
| Amano-Lipase AK (Pseudomonas) | 5.6 | 74 | 167 | 93 | 11372 |

TABLE 4

Enzyme Screen for Hydrolysis/Methanolysis of Butyl-KLG
(38° C. for 47.5 Hours/38% Methanol-Water/0.1 M MES Buffer)

| Enzyme | Measured pH | KLG | MeKLG | ASA | BuKLG (ppm) |
|---|---|---|---|---|---|
| Pig Liver Esterase | 5.3 | 705 | 2720 | 246 | 1368 |
| Pseudomonas cepacia Lipase | 5.5 | 77 | 288 | 46 | 6222 |
| Porcine Pancreatic Lipase | 5.4 | 229 | 613 | 222 | 10899 |
| Candida rugosa Lipase | 5.8 | 104 | 205 | 155 | 5417 |
| Alpha-Chymotrypsin | 5.1 | 82 | 248 | 54 | 6092 |
| Penicillin Acylase | 5.8 | 100 | 1607 | 30 | 6192 |
| Aspergillus niger Lipase | 5.3 | 214 | 391 | 29 | 6470 |
| Mucor meihei Lipase | 5.6 | 54 | 189 | 108 | 7041 |
| ChiroCLEC-CR | 5.5 | 115 | 218 | 99 | 3769 |
| Subtilisin Carlsberg | 5.1 | 3072 | 47 | 0 | 0 |
| Candida antarctica A | 5.4 | 166 | 316 | 35 | 5943 |
| Candida lipolytica Lipase | 5.7 | 150 | 166 | 0 | 6445 |
| Candida antartica B | 5.3 | 2210 | 3520 | 60 | 0 |
| Humicola lanuginosa Lipase | 5.2 | 129 | 241 | 42 | 8017 |
| Bacillus Sp Protease | 5.3 | 3722 | 1940 | 29 | 38 |
| ChiroCLEC-BL protease | 5 | 3744 | 1724 | 54 | 634 |
| ChiroCLEC PC lipase | 5.7 | 108 | 196 | 5 | 4148 |
| Candida Rugosa esterase | 5.6 | 70 | 309 | 61 | 6734 |
| L-1 (Pseudomonas sp)) | 5.4 | 90 | 336 | 11 | 7066 |
| L-2 (Candida antartica B) | 5.5 | 2622 | 3764 | 14 | 913 |
| L-3 (Candida cylindracea) | 5.7 | 88 | 158 | 37 | 10343 |
| L-5 (Candida antartica A) | 5.5 | 153 | 665 | 42 | 4626 |
| L-6 (Pseudomonas sp) | 5.7 | 0 | 379 | 13 | 6183 |
| L-7 (Porcine pancreas) | 5.8 | 94 | 884 | 120 | 5488 |
| L-8 (Humicola sp) | 5.5 | 98 | 219 | 7 | 7299 |
| no enzyme | 5.6 | 75 | 234 | 5 | 5508 |
| no enzyme | 5.5 | 68 | 209 | 6 | 4968 |
| no enzyme | 5.6 | 65 | 277 | 16 | 5320 |

Example 4

Table 4 below illustrates that a variety of acylases, esterases, lipases, and proteases showed appreciable conversion of butyl-KLG to ascorbic acid, MeKLG, and KLG in a 38% methanol-water solution buffered at pH 5 to 5.8 with MES buffer. Pig liver esterase, *Subtilisin Carlsberg* (a protease), Bacillus species protease, ChiroClec™ -BL, and *Candida Antartica* B lipase all show particularly high levels of activity.

Example 5

Table 5 below illustrates that a variety of lipases and proteases showed appreciable conversion of butyl-KLG to ascorbic acid, MeKLG, and KLG in a 38% methanol-water solution buffered at pH 5.7 to 6.1 with MES buffer. On comparison with the other enzymes in this table, Prozyme 6 (a protease from Aspergillus oryzae), Protease 2A (from *Aspergillus oryzae*), and GC899 (a commercial detergent protease from Genencor International) showed higher levels of activity.

TABLE 5

Enzyme Screen for Hydrolysis/Methanolysis of Butyl-KLG
(38° C. for 19 Hours/38% Methanol-Water/0.1 M MES Buffer)

| Enzyme | Comment | Measured pH | KLG | MeKLG | ASA | BuKLG (ppm) |
|---|---|---|---|---|---|---|
| PS30 (Pseudomonas) | Lipase | 5.9 | 83 | 213 | 32 | 10424 |
| GC4 (*Geotricum candidum*) | Lipase | 5.7 | 0 | 166 | 0 | 7475 |
| AK (Pseudomonas) | Lipase | 6 | 27 | 205 | 26 | 9815 |
| G (Penicillium) | Lipase | 5.8 | 0 | 0 | 0 | 9441 |
| Newlase A (Aspergillus) | Protease | 5.9 | 83 | 299 | 6 | 10368 |
| Protease M (Aspergillus) | Protease | 6 | 498 | 1054 | 281 | 6990 |
| Prozyme 6 (Aspergillus) | Protease | 6 | 1489 | 2259 | 0 | 4965 |
| MAP10 (Mucor) | Lipase | 6.1 | 21 | 148 | 145 | 8968 |
| No enzyme | | 5.9 | 71 | 169 | 22 | 9463 |
| No enzyme | | 5.9 | 75 | 191 | 6 | 9391 |
| No enzyme | | 5.9 | 79 | 196 | 7 | 9539 |
| D (Rhizopus) | Lipase | 5.7 | 44 | 156 | 3 | 8562 |
| Newlase II (Rhizopus) | Protease | 5.9 | 36 | 164 | 12 | 9586 |
| AY30 (Candida) | Lipase | 6 | 0 | 192 | 33 | 8725 |
| L-10 (Candida) | Lipase | 5.7 | 0 | 0 | 0 | 9608 |
| CES (Pseudomonas) | Lipase | 5.8 | 52 | 296 | 42 | 9491 |
| N (Rhizopus) | Lipase | 5.8 | 78 | 404 | 27 | 9834 |
| 2A (Protease, Aspergillus) | Protease | 6.1 | 937 | 1158 | 215 | 8951 |
| Hog Pancreatic Lipase | Fluka | 6 | 58 | 529 | 130 | 11114 |
| Lipase (Sigma-1754) | Lipase | 5.8 | 57 | 98 | 47 | 9845 |
| Lipase (Sigma-1754) | Lipase | 5.8 | 46 | 88 | 82 | 9428 |
| Lipase (Sigma-8525) | Lipase | 5.9 | 178 | 222 | 60 | 9041 |
| Lipase (Sigma-1754) | Lipase | 5.7 | 76 | 145 | 89 | 14257 |
| Lipase (Sigma-3126) | Lipase | 5.9 | 90 | 415 | 130 | 12756 |
| F-15 (Rhizopus) | Lipase | 5.8 | 55 | 165 | 14 | 10262 |
| Lipozyme (Novo-Liquid) | Lipase | 6 | 82 | 122 | 160 | 9100 |
| GC899 (protease) | Protease | 5.8 | 791 | 2735 | 312 | 11607 |

Example 6

Table 6 below illustrates that a variety of lipases and proteases showed appreciable conversion of butyl-KLG to ascorbic acid, MeKLG, and KLG in a 8.6% methanol-water solution buffered at a pH of 5.3 to 6 with MES buffer. Protease M (*Aspergillus oryzae*), Prozyme 6 (a protease from *Aspergillus oryzae*), Protease N (Subtilisin), and Protease 2A (*Aspergillus oryzae*) all showed particularly high levels of activity.

TABLE 6

Enzyme Screen for Hydrolysis/Methanolysis of Butyl-KLG
(38° for 19 Hours/8.6% Methanol-Water/0.1 M MES)

| Enzyme | Comment | Measured pH | KLG | MeKLG | ASA | BuKLG (ppm) |
|---|---|---|---|---|---|---|
| PS30 (Pseudomonas) | Lipase | 5.9 | 341 | 163 | 157 | 8363 |
| GC4 (*Geotricum candidum*) | Lipase | 5.9 | 424 | 0 | 8 | 4192 |
| AK (Pseudomonas) | Lipase | 6 | 295 | 432 | 125 | 8255 |
| G (Penicillium) | Lipase | 5.8 | 253 | 323 | 0 | 7678 |
| Newlase A (Aspergillus) | Protease | 5.7 | 692 | 302 | 126 | 13408 |
| R-10 (Penicillium) | Lipase | 6 | 527 | 208 | 583 | 5570 |
| Protease M (Aspergillus) | Protease | 6 | 3650 | 2262 | 328 | 1696 |
| Prozyme 6 (Aspergillus) | Protease | 5.3 | 7207 | 694 | 0 | 0 |
| MAP10 (Mucor) | Lipase | 6 | 369 | 0 | 231 | 8334 |
| No enzyme | | 5.8 | 378 | 239 | 132 | 8272 |
| No enzyme | | 5.8 | 380 | 205 | 19 | 8582 |
| No enzyme | | 5.8 | 382 | 295 | 43 | 8785 |
| D (Rhizopus) | Lipase | 5.9 | 595 | 326 | 76 | 11656 |
| Newlase II (Rhizopus) | Protease | 5.9 | 323 | 212 | 28 | 8535 |
| AY30 (Candida) | Lipase | 5.9 | 330 | 249 | 254 | 10195 |
| L-10 (Candida) | Lipase | 5.8 | 302 | 69 | 55 | 11057 |
| AP12 (Aspergillus) | Lipase | 6 | 1448 | 738 | 129 | 7730 |
| CES (Pseudomonas) | Lipase | 5.9 | 197 | 252 | 0 | 8092 |
| N (Rhizopus) | Lipase | 6 | 582 | 348 | 61 | 9598 |
| N (Protease, Bacillus) | Protease | 5.7 | 1572 | 1289 | 26 | 1822 |
| 2A (Protease, Aspergillus) | Protease | 5.7 | 5891 | 616 | 160 | 764 |
| Hog Pancreatic Lipase | Fluka | 5.8 | 890 | 791 | 158 | 5284 |
| Lipase (Sigma-1754) | Lipase | 5.9 | 283 | 116 | 148 | 6196 |
| Lipase (Sigma-1754) | Lipase | 6 | 348 | 189 | 415 | 8098 |

TABLE 6-continued

Enzyme Screen for Hydrolysis/Methanolysis of Butyl-KLG
(38° for 19 Hours/8.6% Methanol-Water/0.1 M MES)

| Enzyme | Comment | Measured pH | KLG | MeKLG | ASA | BuKLG (ppm) |
|---|---|---|---|---|---|---|
| Lipase (Sigma-8525) | Lipase | 6 | 326 | 93 | 15 | 4112 |
| Lipase (Sigma-1754) | Lipase | 6 | 300 | 150 | 154 | 8057 |
| Lipase (Sigma-3126) | Lipase | 5.8 | 787 | 488 | 99 | 8829 |
| F-15 (Rhizopus) | Lipase | 5.9 | 218 | 124 | 0 | 8682 |
| Lipozyme (Novo-Liquid) | Lipase | 5.8 | 380 | 95 | 101 | 7251 |
| GC899 (protease) | Protease | 5.6 | 3354 | 1765 | 201 | 6991 |

Example 7

Table 7 below illustrates that a variety of acylases, esterases, lipases, and proteases showed appreciable conversion of butyl-KLG to ascorbic acid, MeKLG, and KLG in a 8.6% methanol-water solution buffered at a pH of approximately 5 to 6 with MES buffer. *Candida Antartica* B lipase, pig liver esterase, and Bacillus species protease showed particularly high levels of activity.

TABLE 7

Enzyme Screen for Hydrolysis/Methanolysis of Butyl-KLG
(38° C. for 19 Hours/8.6% Methanol-Water/0.1M MES)

| Enzyme | Comment | KLG | MeKLG | ASA | BuKLG |
|---|---|---|---|---|---|
| L-1 (Pseudomonas sp)) | Lipase | 137 | 116 | 47 | 7601 |
| L-2 (Candida antartica B) | Lipase | 5249 | 1921 | 0 | 768 |
| L-3 (Candida cylindracea) | Lipase | 183 | 64 | 107 | 6920 |
| L-4 (Pseudomonas sp) | Lipase | 239 | 163 | 88 | 9957 |
| L-5 (Candida antartica A) | Lipase | 278 | 344 | 0 | 6245 |
| L-6 (Pseudomonas sp) | Lipase | 90 | 219 | 15 | 6613 |
| L-7 (Porcine pancreas) | Lipase | 1007 | 575 | 106 | 5392 |
| L-8 (Humicola sp) | Lipase | 209 | 70 | 150 | 7957 |
| no enzyme | | 168 | 152 | 6 | 8753 |
| no enzyme | | 152 | 144 | 3 | 8233 |
| no enzyme | | 170 | 137 | 18 | 8157 |
| ESL-001-01 | Recombinant | 1271 | 906 | 375 | 4635 |
| ESL-001-02 | Biocatalysis | 883 | 329 | 332 | 5949 |
| ESL-001-03 | Enzymes | 290 | 123 | 447 | 7333 |
| ESL-001-04 | | 511 | 161 | 306 | 6207 |
| ESL-001-05 | | 364 | 124 | 299 | 6402 |
| ESL-001-06 | | 329 | 117 | 118 | 6934 |
| ESL-001-07 | | 0 | 122 | 430 | 15752 |
| Pig Liver Esterase | | 2726 | 3731 | 423 | 10 |
| Pseudomonas cepacia Lipase | | 241 | 109 | 224 | 9135 |
| Porcine Pancreatic Lipase | | 333 | 291 | 314 | 7888 |
| Candida rugosa Lipase | | 296 | 86 | 451 | 8697 |
| no enzyme | | 153 | 116 | 8 | 8234 |
| Alpha-Chymotrypsin | protease | 330 | 1076 | 65 | 3855 |
| Penicillin Acylase | | 187 | 1248 | 157 | 8110 |
| no enzyme | | 100 | 73 | 3 | 5296 |
| no enzyme | | 144 | 113 | 7 | 8106 |
| Aspergillus niger Lipase | | 479 | 72 | 84 | 8455 |
| Mucor meihei Lipase | | 229 | 278 | 156 | 8620 |
| ChiroCLEC-CR | lipase | 233 | 155 | 11 | 7569 |
| Subtilisin Carlsberg | | 4463 | 93 | 0 | 4428 |
| Candida antarctica A | lipase | 215 | 0 | 175 | 7573 |
| Candida lipolytica Lipase | | 198 | 62 | 92 | 8445 |
| Bacillus Sp Protease | | 4920 | 642 | 13 | 72 |
| ChiroCLEC-BL protease | | 2860 | 1233 | 135 | 4051 |
| ChiroCLEC PC lipase | | 127 | 62 | 2 | 5653 |
| Candida Rugosa esterase | | 178 | 120 | 225 | 9382 |

Example 8

Table 8 below illustrates that a variety of acylases, esterases, lipases, and proteases showed appreciable conversion of butyl-KLG to ascorbic acid, MeKLG, and KLG in a 8.6% methanol-water solution buffered at a pH of approximately 5.8 to 6.2 with MES buffer. Pig liver esterase, *Candida Antartica* B lipase, Bacillus species protease, and lightly crosslinked crystalline Subtilisin (ChirClec-BL) showed particularly high levels of activity.

TABLE 8

Enzyme Screen for Hydrolysis/Methanolysis of Butyl-KLG
(38° C. for 21 Hours/8.6% Methanol-Water/0.2M MES

| Enzyme | Comment | pH | KLG | MeKLG | ASA | BuKLG (ppm) |
|---|---|---|---|---|---|---|
| Pig Liver Esterase | | 5.8 | 2373 | 4167 | 717 | 83 |
| *Pseudomonas cepacia* Lipase | | 5.9 | 173 | 169 | 25 | 7384 |
| Porcine Pancreatic Lipase | | 5.9 | 303 | 320 | 78 | 6860 |
| *Candida rugosa* Lipase | | 5.9 | 260 | 112 | 271 | 7351 |
| Alpha-Chymotrypsin | protease | 5.9 | 506 | 1239 | 146 | 4707 |
| Penicillin Acylase | | 6 | 176 | 1172 | 98 | 5392 |
| *Aspergillus niger* Lipase | | 5.9 | 493 | 259 | 84 | 6364 |
| *Mucor meihei* Lipase | | 5.9 | 243 | 283 | 54 | 7067 |
| no enzyme | | 5.9 | 198 | 173 | 2 | 7137 |
| no enzyme | | 5.9 | 216 | 153 | 0 | 7115 |
| no enzyme | | 5.9 | 223 | 154 | 1 | 7319 |
| *Candida Antartica* 'A' Lipase | | 5.9 | 222 | 142 | 148 | 6683 |
| *Candida lipolytica* Lipase | | 6 | 721 | 123 | 25 | 6721 |
| *Candida antartica* 'B' Lipase | | 5.9 | 2708 | 709 | 20 | 28 |
| *Humicola lanuginosa* Lipase | | 5.9 | 176 | 129 | 10 | 7215 |
| Bacillus Species Protease | | 5.8 | 5553 | 603 | 0 | 33 |
| ChiroCLEC-CR (Dry) | | 6.1 | 229 | 170 | 2 | 7191 |
| ChiroCLEC-BL (Dry) | | 5.9 | 4293 | 1282 | 6 | 1376 |
| ChiroCLEC-PC (*P. cepacia*-Dry) | | 6.1 | 240 | 268 | 2 | 7539 |
| *Rhizoipus Delmar* Lipase | | 6 | 178 | 0 | 0 | 7097 |
| *Rhizopus Niveus* Lipase | | 6.2 | 178 | 181 | 61 | 7102 |
| *Rhizopus Oryzae* Lipase | | 6.1 | 159 | 119 | 26 | 7611 |
| *Chromobacterium Viscosum* Lipase | | 6 | 415 | 181 | 2 | 7275 |
| *Geotricum Candidum* Lipase | | 6.1 | 146 | 122 | 6 | 6140 |
| *Mucor Javanicus* Lipase | | 6.2 | 167 | 95 | 141 | 7422 |
| *Aspergillus Oryzae* Protease | | 6.1 | 2193 | 1462 | 39 | 2904 |
| *Candida Rugosa* Esterase | | 5.8 | 129 | 132 | 17 | 7164 |

Example 9

Table 9 below demonstrates the statistical reproduction of the activity detected for highly active enzymes in the preceding examples. Eight of the enzymes from the previous examples, which were identified as showing particularly high levels of activity, were compared under tight pH control. All of the previously identified enzymes with high levels of activity maintained this high level of activity on reanalysis. The enzymes exhibited appreciable conversion of butyl-KLG to ascorbic acid, MeKLG, and KLG in a 8.6% methanol-water solution buffered at a pH of approximately 5.6 to 6 with 0.2 M MES buffer. *Candida Antartica* B lipase, pig liver esterase, and Bacillus species protease showed particularly high levels of activity within this comparative example. Pig liver esterase showed a selectivity toward transesterification as well as significant conversions to ascorbic acid.

TABLE 9

Enzyme Screen for Hydrolysis/Methanolysis of Butyl-KLG
(38° C. for 19 Hours/8.6% Metanol-Water/0.2 M MES Buffer)

| Enzyme | Comment | PH | KLG | MeKLG | ASA | BuKLG (ppm) |
|---|---|---|---|---|---|---|
| N Protease | Protease | 6 | 700 | 1166 | 297 | 5435 |
| *Candida Antartica* B | Lipase | 5.8 | 4347 | 2207 | 283 | 0 |
| Pig Liver Esterase | Esterase | 5.9 | 1947 | 4258 | 650 | 0 |
| Bacillus sp Protease | Protease | 5.6 | 5137 | 745 | 55 | 0 |
| ChiroClec-BL (Dry) | Subtilisin | 5.8 | 3485 | 1235 | 215 | 3045 |
| Prozyme-6 | Protease | 5.8 | 3405 | 1518 | 73 | 1624 |
| Protease M | Protease | 6 | 554 | 668 | 271 | 6329 |
| 2A Protease | Protease | 5.9 | 1585 | 1501 | 153 | 3954 |
| no enzyme | | 6 | 135 | 149 | 14 | 8170 |
| no enzyme | | 5.9 | 136 | 127 | 16 | 8418 |
| no enzyme | | 6 | 142 | 133 | 13 | 8570 |

Example 10

Table 10 below compares the same enzymes as in Example 9 except at a higher concentration of organic solvent. *Candida Antartica* B and Bacillus species protease showed particularly high levels of activity in that they exhibited appreciable conversion of butyl-KLG to ascorbic acid, MeKLG, and KLG in a 38% methanol-water solution buffered at a pH of approximately 5.6 to 6.2 with 0.2 M MES buffer. Decreased, although still appreciable, activity is observed for pig liver esterase relative to that shown in Example 9.

TABLE 10

Enzyme Screen for Hydrolysis/Methanolysis of Butyl-KLG
(38° C. for 19 Hours/38% Methanol-Water/0.2 M MES Buffer)

| Enzyme | Comment | pH | KLG | MeKLG | ASA | BuKLG (ppm) |
|---|---|---|---|---|---|---|
| N Protease | Protease | 5.9 | 176 | 1144 | 126 | 8153 |
| *Candida Antartica* B | Lipase | 5.8 | 1701 | 5710 | 213 | 199 |
| Pig Liver Esterase | Esterase | 6 | 203 | 1654 | 173 | 7030 |
| Bacillus sp Protease | Protease | 5.6 | 3104 | 4032 | 182 | 213 |
| Chiroclec-BL (Dry) | Protease | 5.8 | 1261 | 1693 | 102 | 5572 |
| Prozyme-6 | Protease | 6 | 350 | 1268 | 47 | 7517 |
| Protease M | Protease | 6.2 | 141 | 408 | 199 | 9400 |
| 2A Protease | Protease | 6.1 | 178 | 626 | 90 | 8666 |
| no enzyme | | 6 | 69 | 221 | 8 | 9418 |
| no enzyme | | 5.9 | 61 | 189 | 7 | 8790 |
| no enzyme | | 6 | 63 | 203 | 9 | 9367 |

Example 11

Table 11 below compares the same enzymes as in Example 9 except at a pH buffered around 5.2. *Candida Antartica* B and pig liver esterase showed particularly high levels of activity in that they exhibited appreciable conversion of butyl-KLG to MeKLG and KLG in a 8.6% methanol-water solution buffered at a pH of approximately 4.9 to 5.3 with 0.2 M pyridine/pyridinium hydrochloride buffer. Decreased, although still appreciable, activity is observed for Bacillus species protease relative to Example 9.

TABLE 11

Enzyme Screen for Hydrolysis/Methanolysis of BUKLG
(38° C. for ca 19 Hours/8.6% Methanol-Water/0.2 M Pyridine/
Pyridiniuym Hydrochloride)

| Enzyme | Comment | pH | KLG | MeKLG | ASA | BuKLG (ppm) |
|---|---|---|---|---|---|---|
| N Protease | Protease | 5.2 | 87 | 237 | 47 | 8320 |
| *Candida Antartica* B | Lipase | 4.9 | 3460 | 3097 | 53 | 0 |
| Pig Liver Esterase | Esterase | 5.2 | 1613 | 5787 | 37 | 390 |
| Bacillus sp Protease | Protease | 5.1 | 1613 | 2473 | 70 | 3757 |
| ChiroClec-BL (Dry) | Protease | 5.1 | 987 | 1360 | 67 | 5603 |
| Prozyme-6 | Protease | 5.2 | 700 | 840 | 7 | 6470 |
| Protease M | Protease | 5.3 | 187 | 357 | 0 | 8387 |
| 2A Protease | Protease | 5.2 | 480 | 643 | 0 | 7523 |
| no enzyme | | 5.3 | 97 | 0 | 153 | 9750 |
| no enzyme | | 5,2 | 73 | 0 | 80 | 9547 |

Example 12

Table 12 below compares the same enzymes as in Example 11 except at a higher concentration of organic solvent. *Candida Antartica* B showed particularly high levels of activity in that it exhibited appreciable conversion of butyl-KLG to MeKLG and KLG in 38% methanol-water solution buffered at a pH of approximately 4.7 to 5.1 with 0.2 M pyridine/pyridinium hydrochloride buffer. All of the enzymes showed reduced activity relative to Examples 9 and 11.

TABLE 12

Enzyme Screen for Hydrolysis/Methanolysis of BuKLG
(38° C. for ca. 19 Hours/H 4.9/38% Methanol-Water)

| Enzyme | Comment | PH | KLG | MeKLG | ASA | BuKLG |
|---|---|---|---|---|---|---|
| N Protease | Protease | 4.8 | 0 | 0 | 17 | 9093 |
| Candida Antartica B | Lipase | 4.7 | 1953 | 6470 | 0 | 5373 |
| Pig Liver Esterase | Esterase | 4.9 | 47 | 197 | 0 | 11750 |
| Bacillus sp Protease | Protease | 4.9 | 333 | 2113 | 30 | 10043 |
| ChiroClec-BL (Dry) | Protease | 4.9 | 97 | 447 | 7 | 10950 |
| Prozyme-6 | Protease | 4.9 | 0 | 113 | 3 | 12730 |

TABLE 12-continued

Enzyme Screen for Hydrolysis/Methanolysis of BuKLG
(38° C. for ca. 19 Hours/H 4.9/38% Methanol-Water)

| Enzyme | Comment | PH | KLG | MeKLG | ASA | BuKLG |
|---|---|---|---|---|---|---|
| Protease M | Protease | 5.1 | 73 | 203 | 0 | 15887 |
| 2A Protease | Protease | 5 | 67 | 150 | 0 | 13920 |
| no enzyme | | 4.9 | 87 | 13 | 27 | 11753 |

Example 13

Table 13 below compares the same enzymes as in Examples 9 and 11 except at a pH buffered around 2.3. All enzymes tested showed reduced activity relative to Examples 9 and 11 for conversion of butyl-KLG to ascorbic acid, MeKLG, and KLG in a 8.6% methanol-water solution buffered at a pH of approximately 2.3–2.7 with 0.2 M phosphate buffer.

TABLE 13

Enzyme Screen for Hydrolysis/Methanolysis of BuKLG (38° C. for 20 Hours/8.6% Methanol-Water/pH 2.3 0.2M Phosphate Buffer)

| Enzyme | Comment | PH | KLG | MeKLG | ASA | BuKLG |
|---|---|---|---|---|---|---|
| N Protease | Protease | 2.4 | 203 | 0 | 3 | 8980 |
| Candida Antartica B | Lipase | 2.4 | 397 | 323 | 0 | 8463 |
| Pig Liver Esterase | Esterase | 2.4 | 417 | 93 | 0 | 9500 |
| Bacillus sp Protease | Protease | 2.3 | 347 | 0 | 0 | 10987 |
| ChiroClec-BL (Dry) | Protease | 2.3 | 387 | 0 | 0 | 10580 |
| Prozyme-6 | Protease | 2.4 | 440 | 0 | 0 | 12357 |
| Protease N | Protease | 2.6 | 137 | 333 | 0 | 12237 |
| 2A Protease | Protease | 2.7 | 163 | 347 | 0 | 10600 |
| No enzyme | | 2.3 | 487 | 0 | 0 | 10417 |
| No enzyme | | 2.3 | 413 | 0 | 0 | 9897 |
| No enzyme | | 2.3 | 407 | 0 | 0 | 9873 |

Example 14

Table 14 below compares the first 5 enzymes of Examples 9 and 11 at a buffered pH of about 6 in their ability to catalyze the esterification of KLG to methyl KLG (MeKLG) or their ability to catalyze ring closure of KLG to ascorbic acid. Low levels of activity are observed relative to examples 9 and 11.

TABLE 14

Enzyme Screen for Methanolysis of KLG
(38° C. for 19 Hours/8.6% Methanol-Water/0.2M MES Buffer)

| Enzyme | Comment | PH | KLG | MeKLG | ASA | BuKLG |
|---|---|---|---|---|---|---|
| N Protease | Protease | 6 | 3791 | 0 | 0 | 0 |
| Candida Antartica B | Lipase | 6 | 4258 | 0 | 0 | 0 |
| Pig Liver Esterase | Esterase | 6 | 4393 | 0 | 0 | 0 |
| Bacillus sp Protease | Protease | 6 | 4099 | 0 | 0 | 0 |
| ChiroClec-BL (Dry) | Subtilisin | 6.1 | 3270 | 0 | 0 | 0 |
| no enzyme | | 6 | 4340 | 0 | 0 | 0 |
| no enzyme | | 6 | 3295 | 0 | 0 | 0 |
| no enzyme | | 6 | 4029 | 0 | 0 | 0 |

Example 15

Table 15 below demonstrates the production of MeKLG from KLG using Candida Antartica B lipase as catalyst in 8.6% aqueous methanol at a pH of 3–3.2. The buffer was chosen as a mixture of KLG and its sodium salt (approximately ⅛). The first three entries include enzyme catalyst and are the same conditions in triplicate. The second three entries also run in triplicate and are the same conditions as the first three entries except that no enzyme was present. The first three entries show significant esterification of KLG to MeKLG in the presence of *Candida Antartica* B lipase. The second three entries demonstrate that the conversion does not proceed in the absence of *Candida Antartica* B lipase.

TABLE 15

Enzyme Screen for Esterification of KLG
68 Hours at 38° C./8.6% Methanol in Aqueous Phase/Buffer = KLG + NaKLG

| Enzyme | Comment | pH | KLG | MeKLG | ASA | BuKLG |
|---|---|---|---|---|---|---|
| *Candida Antartica* B | 8.6% MeOH + KLG | 3.1 | 9227 | 460 | 0 | 0 |
| *Candida Antartica* B | 8.6% MeOH + KLG | 3.1 | 9303 | 530 | 0 | 0 |
| *Candida Antartica* B | 8.6% MeOH + KLG | 3.2 | 9213 | 413 | 0 | 0 |
| no enzyme | 8.6% MeOH + KLG | 2.9 | 9530 | 0 | 0 | 0 |
| no enzyme | 8.6% MeOH + KLG | 2.9 | 9477 | 0 | 0 | 0 |
| no enzyme | 8.6% MeOH + KLG | 2.9 | 9600 | 0 | 0 | 0 |

Example 16

This example demonstrates the slow decomposition of ascorbic acid under the conditions of HPLC analysis. HPLC sample standards were prepared by dissolving KLG, MeKLG, ascorbic acid (ASA), and butyl-KLG to the appropriate concentration in water. Samples of these standards were placed in filled and sealed vials, stored at room temperature, and analyzed periodically. The HPLC was calibrated on the area response for standards that were injected onto the HPLC as soon as possible after the preparation of the standards. Table 16 below shows the recorded responses for KLG, MeKLG, ascorbic acid, and butyl-KLG standards of 50, 100, and 500 ppm at time 0 (calibration time), at approximately 6.5 hours, and at approximately 12 hours after sample preparation.

TABLE 16

| Time (minutes) | Amount Prepared | Amount Found KLG | MeKLG | ASA | BuKLG |
|---|---|---|---|---|---|
| 0 | 50 ppm standard | 51 | 51.4 | 53.4 | 50.6 |
| 400 | | 39.9 | 47.7 | 28.3 | 42.7 |
| 715 | | 52 | 43 | 0 | 38.2 |
| 0 | 100 ppm standard | 102 | 103 | 107 | 101 |
| 400 | | 94.3 | 106.8 | 96.6 | 100.1 |
| 715 | | 81.8 | 90.2 | 57.2 | 94.2 |
| 0 | 500 ppm standard | 510 | 514 | 534 | 506 |

TABLE 16-continued

| Time (minutes) | Amount Prepared | Amount Found KLG | MeKLG | ASA | BuKLG |
|---|---|---|---|---|---|
| 400 | | 479 | 496 | 487 | 512 |
| 715 | | 493 | 495 | 473 | 499 |

The ascorbic acid responses were non-linear over time with respect to the other standards and, particularly, with respect to standards of 100 ppm or less. Given that the treatment for Examples 2–16 included approximately 16 hours or more at 38° C. on a shaker bath prior to HPLC analysis, it follows that the actual level of ascorbic acid formed was greater than reported.

This invention has been described in detail with particular reference to preferred embodiments thereof, but it will be understood that variations and modifications can be effected within the spirit and scope of the invention.

SEQ ID NO: 1

SEQ ID NO: 2

SEQ ID NO: 3

What is claimed is:

1. A process for preparing 2-keto-L-gulonic acid comprising the steps of:

(a) preparing an aqueous solution of an ester of 2-keto-L-gulonic acid, and (b) then contacting the ester of 2-keto-L-gulonic acid in solution with a hydrolase enzyme catalyst to form 2-keto-L-gulonic acid.

2. The process of claim 1 wherein the hydrolase enzyme catalyst is selected from the group consisting of a protease, an esterase, a lipase and an amidase.

3. The process of claim 1 wherein a co-solvent is used in preparing the aqueous solution.

4. The process of claim 3 wherein the co-solvent is a $C_1$ to $C_6$ alcohol.

* * * * *

UNITED STATES PATENT AND TRADEMARK OFFICE
CERTIFICATE OF CORRECTION

PATENT NO. : 6,022,719

DATED : February 8, 2000

INVENTOR(S) : John Clark Hubbs

It is certified that error appears in the above-identified patent and that said Letters Patent is hereby corrected as shown below:

On the second page, after CROSS REFERENCE TO RELATED APPLICATIONS section, column 1, line 13, add:

"GOVERNMENT LICENSE RIGHTS

This invention was made with United States Government support under Cooperative Research Agreement No. 70NANB5H1138 awarded by the Advanced Technology Program of the National Institute of Standards and Technology. The United States Government has certain rights in the invention."

Signed and Sealed this

Eighth Day of May, 2001

*Attest:*

NICHOLAS P. GODICI

*Attesting Officer*   Acting Director of the United States Patent and Trademark Office

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 379 amino acids
      (B) TYPE: Amino Acid
      (D) TOPOLOGY: Linear (ii) MOLECULE TYPE: protein (xi) SEQUENCE DESCRIPTION: SEQ ID NO:1:

```
Met Met Arg Lys Lys Ser Phe Trp Leu Gly Met Leu Thr Ala Phe Met
 1               5                  10                  15

Leu Val Phe Thr Met Ala Phe Ser Asp Ser Ala Ser Ala Ala Gln Pro
                20                  25                  30

Ala Lys Asn Val Glu Lys Asp Tyr Ile Val Gly Phe Lys Ser Gly Val
            35                  40                  45

Lys Thr Ala Ser Val Lys Lys Asp Ile Ile Lys Glu Ser Gly Gly Lys
        50                  55                  60

Val Asp Lys Gln Phe Arg Ile Ile Asn Ala Ala Lys Ala Lys Leu Asp
 65                 70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
                100                 105                 110

Ile Pro Leu Ile Lys Ala Asp Lys Val Gln Ala Gln Gly Phe Lys Gly
```

-continued

```
            115                 120                 125
Ala Asn Val Lys Val Ala Val Leu Asp Thr Gly Ile Gln Ala Ser His
        130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
                180                 185                 190

Ser Leu Tyr Ala Val Lys Val Leu Asn Ser Ser Gly Ser Gly Thr Tyr
            195                 200                 205

Ser Gly Ile Val Ser Gly Ile Glu Trp Ala Thr Thr Asn Gly Met Asp
        210                 215                 220

Val Ile Asn Met Ser Leu Gly Gly Pro Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
                260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
        290                 295                 300

Pro Gly Ala Gly Val Tyr Ser Thr Tyr Pro Thr Ser Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
                340                 345                 350

Arg Leu Ser Ser Thr Ala Thr Tyr Leu Gly Ser Ser Phe Tyr Tyr Gly
            355                 360                 365

Lys Gly Leu Ile Asn Val Glu Ala Ala Ala Gln
370                 375

(2) INFORMATION FOR SEQ ID NO:2:

(i) SEQUENCE CHARACTERISTICS:
        (A) LENGTH:  584 amino acids
        (B) TYPE: Amino Acid
        (D) TOPOLOGY:  Linear (ii) MOLECULE TYPE:  protein (xi) SEQUENCE DESCRIPTION: SEQ ID NO:2:

Met Trp Leu Leu Pro Leu Val Leu Thr Ser Leu Ala Ser Ser Ala Thr
1               5                   10                  15

Trp Ala Gly Gln Pro Ala Ser Pro Pro Val Val Asp Thr Ala Gln Gly
            20                  25                  30

Arg Val Leu Gly Lys Tyr Val Ser Leu Glu Gly Leu Ala Phe Thr Gln
        35                  40                  45

Pro Val Ala Val Phe Leu Gly Val Pro Phe Ala Lys Pro Pro Leu Gly
    50                  55                  60

Ser Leu Arg Phe Ala Pro Pro Gln Pro Ala Glu Pro Trp Ser Phe Val
65                  70                  75                  80

Lys Asn Thr Thr Ser Tyr Pro Pro Met Cys Cys Gln Asp Pro Val Val
                85                  90                  95
```

-continued

```
Glu Gln Met Thr Ser Asp Leu Phe Thr Asn Phe Thr Gly Lys Glu Arg
            100                 105                 110

Leu Thr Leu Glu Phe Ser Glu Asp Cys Leu Tyr Leu Asn Ile Tyr Thr
        115                 120                 125

Pro Ala Asp Leu Thr Lys Arg Gly Arg Leu Pro Val Met Val Trp Ile
130                 135                 140

His Gly Gly Gly Leu Val Leu Gly Gly Ala Pro Met Tyr Asp Gly Val
145                 150                 155                 160

Val Leu Ala Ala His Glu Asn Phe Thr Val Val Val Ala Ile Gln
                165                 170                 175

Tyr Arg Leu Gly Ile Trp Gly Phe Phe Ser Thr Gly Asp Glu His Ser
                180                 185                 190

Arg Gly Asn Trp Gly His Leu Asp Gln Val Ala Ala Leu His Trp Val
            195                 200                 205

Gln Glu Asn Ile Ala Asn Phe Gly Gly Asp Pro Gly Ser Val Thr Ile
        210                 215                 220

Phe Gly Glu Ser Phe Thr Ala Gly Gly Glu Ser Val Ser Val Leu Val
225                 230                 235                 240

Leu Ser Pro Leu Ala Lys Asn Leu Phe His Arg Ala Ile Ser Glu Ser
                245                 250                 255

Gly Val Ala Leu Thr Val Ala Leu Val Arg Lys Asp Met Lys Ala Ala
            260                 265                 270

Ala Lys Gln Ile Ala Val Leu Ala Gly Cys Lys Thr Thr Thr Ser Ala
        275                 280                 285

Val Phe Thr Phe Val His Cys Leu Arg Gln Lys Ser Glu Asp Glu Leu
290                 295                 300

Leu Asp Leu Thr Leu Lys Met Lys Phe Leu Thr Leu Asp Phe His Gly
305                 310                 315                 320

Asp Gln Arg Glu Ser His Pro Phe Leu Pro Thr Val Val Asp Gly Val
                325                 330                 335

Leu Leu Pro Lys Met Pro Glu Glu Ile Leu Ala Glu Lys Asp Phe Thr
            340                 345                 350

Phe Asn Thr Val Pro Tyr Ile Val Gly Ile Asn Lys Gln Glu Phe Gly
        355                 360                 365

Trp Leu Leu Pro Thr Met Met Gly Phe Pro Leu Ser Glu Gly Lys Leu
370                 375                 380

Asp Gln Lys Thr Ala Thr Ser Leu Leu Trp Lys Ser Tyr Pro Ile Ala
385                 390                 395                 400

Asn Ile Pro Glu Glu Leu Thr Pro Val Ala Thr Phe Thr Asp Lys Tyr
                405                 410                 415

Leu Gly Gly Thr Asp Asp Pro Val Lys Lys Asp Leu Phe Leu Asp
            420                 425                 430

Leu Met Gly Asp Val Val Phe Gly Val Pro Ser Val Thr Val Ala Arg
        435                 440                 445

Gln His Arg Asp Ala Gly Ala Pro Thr Tyr Met Tyr Glu Phe Gln Tyr
450                 455                 460

Arg Pro Ser Phe Ser Ser Asp Lys Phe Thr Lys Pro Lys Thr Val Ile
465                 470                 475                 480

Gly Asp His Gly Asp Glu Ile Phe Ser Val Phe Gly Phe Pro Leu Leu
                485                 490                 495

Lys Gly Asp Ala Pro Glu Glu Val Ser Leu Ser Lys Thr Val Met
            500                 505                 510

Lys Phe Trp Ala Asn Phe Ala Arg Ser Gly Asn Pro Asn Gly Glu Gly
        515                 520                 525
```

```
Leu Pro His Trp Pro Phe Thr Met Tyr Asp Gln Glu Glu Gly Tyr Leu
        530                 535                 540

Gln Ile Gly Val Asn Thr Gln Ala Ala Lys Arg Leu Lys Gly Glu Glu
545                 550                 555                 560

Val Ala Phe Trp Asn Asp Leu Leu Ser Lys Glu Ala Ala Lys Lys Pro
                565                 570                 575

Pro Lys Ile Lys His Ala Glu Leu
        580
```

(2) INFORMATION FOR SEQ ID NO:3:

(i) SEQUENCE CHARACTERISTICS:
        (A) LENGTH: 342 amino acids
        (B) TYPE: Amino Acid
        (D) TOPOLOGY: Linear (ii) MOLECULE TYPE: protein (xi) SEQUENCE DESCRIPTION: SEQ ID NO:3:

```
Met Lys Leu Leu Ser Leu Thr Gly Val Ala Gly Val Leu Ala Thr Cys
 1               5                  10                  15

Val Ala Ala Thr Pro Leu Val Lys Arg Leu Pro Ser Gly Ser Asp Pro
                20                  25                  30

Ala Phe Ser Gln Pro Lys Ser Val Leu Asp Ala Gly Leu Thr Cys Gln
            35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
                100                 105                 110

Thr Ala Leu Tyr Ala Gly Ser Gly Asn Asn Lys Leu Pro Val Leu Thr
            115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Gly Ser Ala Leu Thr Thr Ala Leu
            180                 185                 190

Arg Asn Ala Gly Gly Leu Thr Gln Ile Val Pro Thr Thr Asn Leu Tyr
    195                 200                 205

Ser Ala Thr Asp Glu Ile Val Gln Pro Gln Val Ser Asn Ser Pro Leu
210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
    275                 280                 285

Asn Asp Leu Thr Pro Glu Gln Lys Val Ala Ala Ala Leu Leu Ala
```

```
              290                 295                 300
Pro Ala Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
                340
```